United States Patent
Kobal et al.

(10) Patent No.: US 10,799,548 B2
(45) Date of Patent: *Oct. 13, 2020

(54) MODIFYING TASTE AND SENSORY IRRITATION OF SMOKELESS TOBACCO AND NON-TOBACCO PRODUCTS

(71) Applicant: Altria Client Services LLC, Richmond, VA (US)

(72) Inventors: Gerd Kobal, Sandy Hook, VA (US); Georgios D. Karles, Richmond, VA (US); Munmaya K. Mishra, Manakin Sabot, VA (US)

(73) Assignee: Altria Client Services LLC, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/206,454

(22) Filed: Mar. 12, 2014

(65) Prior Publication Data

US 2014/0271946 A1    Sep. 18, 2014

Related U.S. Application Data

(60) Provisional application No. 61/800,099, filed on Mar. 15, 2013.

(51) Int. Cl.

| | | |
|---|---|---|
| *A61K 36/47* | (2006.01) | |
| *A24B 13/00* | (2006.01) | |
| *A61K 45/06* | (2006.01) | |
| *A61K 31/23* | (2006.01) | |
| *A61K 31/231* | (2006.01) | |
| *A24B 15/32* | (2006.01) | |
| *A61K 31/201* | (2006.01) | |
| *A61K 31/465* | (2006.01) | |
| *A61K 31/20* | (2006.01) | |
| *A61K 31/765* | (2006.01) | |

(52) U.S. Cl.
CPC .............. *A61K 36/47* (2013.01); *A24B 13/00* (2013.01); *A24B 15/32* (2013.01); *A61K 31/20* (2013.01); *A61K 31/201* (2013.01); *A61K 31/23* (2013.01); *A61K 31/231* (2013.01); *A61K 31/465* (2013.01); *A61K 31/765* (2013.01); *A61K 45/06* (2013.01)

(58) Field of Classification Search
CPC ............................... A61K 36/47; A24B 13/00
See application file for complete search history.

(56) References Cited

U.S. PATENT DOCUMENTS

| | | | |
|---|---|---|---|
| 4,528,993 A | | 7/1985 | Sensabaugh et al. |
| 4,597,961 A | | 7/1986 | Etscorn |
| 4,660,577 A | | 4/1987 | Sensabaugh et al. |
| 4,848,373 A | | 7/1989 | Lenkey |
| 4,946,782 A | * | 8/1990 | Farbood ............... A24B 15/403 |
| | | | 435/123 |
| 5,372,149 A | | 12/1994 | Roth et al. |
| 5,487,902 A | * | 1/1996 | Andersen ................. A23G 4/00 |
| | | | 426/3 |
| 6,306,372 B1 | | 10/2001 | Stier et al. |
| 6,676,959 B1 | * | 1/2004 | Andersson et al. .......... 424/435 |
| 6,713,051 B2 | | 3/2004 | Mayes et al. |
| 7,429,673 B2 | | 9/2008 | Morazzoni et al. |
| 2002/0173485 A1 | * | 11/2002 | Mastradonato et al. ........ 514/54 |
| 2004/0118422 A1 | | 6/2004 | Lundin et al. |
| 2005/0118267 A1 | | 6/2005 | Baichwal et al. |
| 2005/0178398 A1 | | 8/2005 | Breslin et al. |
| 2005/0252809 A1 | * | 11/2005 | Aldridge ................ B65D 5/009 |
| | | | 206/449 |
| 2006/0198873 A1 | * | 9/2006 | Chan et al. .................... 424/443 |
| 2007/0128311 A1 | * | 6/2007 | Prakash ................ A23L 1/2366 |
| | | | 426/3 |
| 2008/0286340 A1 | | 11/2008 | Andersson et al. |
| 2009/0004275 A1 | * | 1/2009 | Martyn .................. A61K 9/006 |
| | | | 514/1.1 |
| 2009/0111732 A1 | | 4/2009 | Domb |
| 2009/0196834 A1 | * | 8/2009 | Andersen ......................... 424/48 |
| 2010/0092425 A1 | | 4/2010 | Andrian et al. |
| 2010/0163062 A1 | | 7/2010 | Atchley et al. |

(Continued)

FOREIGN PATENT DOCUMENTS

| | | |
|---|---|---|
| CN | 201171341 | 12/2008 |
| CN | 201171341 Y | 12/2008 |

(Continued)

OTHER PUBLICATIONS

"IARC Monographs". vol. 89: Smokeless Tobacco and Some Tobacco-specific N-nitrosamines. Lyon France. p. 50. (Year: 2007).*

Seedman. <Retrieved from URL: https://web.archive.org/web/20120310140436/https://www.seedman.com/flavor.htm>. (Year: 2012 ).*

Delta Dental. "It may be smokeless, but it's still tobacco". Retrieved from the Internet on: Jan. 17, 2019. Retrieved from the Internet:: < URL: https://www.deltadentalins.com/oral_health/smokelesstobacco.html>. (Year: 2011).*

Tso, Chapter 1 in Tobacco: Production, Chemistry and Technology 1-31 (1991).

(Continued)

Primary Examiner — Amy L Clark

(74) Attorney, Agent, or Firm — Harness, Dickey & Pierce, P.L.C.

(57) ABSTRACT

Tobacco products comprising smokeless tobacco products and active ingredients, including those that antagonize nicotinic acetylcholine receptors, the TRPV1 channel, and/or the TRPA1 channel are disclosed. Nicotine replacement therapies comprising active ingredients, including those that antagonize nicotinic acetylcholine receptors, the TRPV1 channel, and/or the TRPA1 channel. The active ingredient may reduce or eliminate sensory irritation arising due to use of the product. Analgesic compositions comprising active ingredients. Methods of reducing taste and sensory irritation by employing an active ingredient.

3 Claims, No Drawings

(56) References Cited

U.S. PATENT DOCUMENTS

| | | |
|---|---|---|
| 2010/0189770 A1 | 7/2010 | Crutchley et al. |
| 2011/0104218 A1 | 5/2011 | Karles et al. |
| 2011/0274628 A1 | 11/2011 | Borschke |
| 2012/0039981 A1* | 2/2012 | Pedersen .............. A61K 9/0058 424/440 |
| 2012/0199149 A1 | 8/2012 | Strickland et al. |

FOREIGN PATENT DOCUMENTS

| | | | |
|---|---|---|---|
| EP | 2 529 634 | 12/2012 | |
| JP | 2010/150163 | 7/2010 | |
| JP | 201050163 | 7/2010 | |
| JP | 2012/148998 | 8/2012 | |
| JP | 2012148998 | 8/2012 | |
| WO | WO-9724036 A1 * | 7/1997 | ............. A23G 4/126 |
| WO | WO 99/16435 | 4/1999 | |
| WO | WO 9916435 A1 * | 4/1999 | ............. A61K 31/20 |
| WO | WO 00/56281 | 9/2000 | |
| WO | WO 03/039518 | 5/2003 | |
| WO | WO-2004075877 A1 * | 9/2004 | ........... A61K 9/0056 |
| WO | WO-2006013416 A1 * | 2/2006 | ........... A61K 9/0056 |
| WO | WO 2011/092653 | 8/2011 | |

OTHER PUBLICATIONS

Annex to Form PCT/ISA/206 Communication Relating to the Results of the Partial International Search issued in PCT/2014/025724 (Aug. 4, 2014).

Calixto et al., Contribution of natural products to the discovery of the transient receptor potential (TRP) channels family and their function, 106 Pharmacology & Therapeutics 179-208 (2005).

Yaguchi et al., Effects of cis-unsaturated free fatty acids on PCK-ε activation and nicotinic ACh receptor responses, 133 Molecular Brain Research 320-324 (2005).

International Search Report for PCT/US2014/025724 dated Oct. 17, 2014.

* cited by examiner

MODIFYING TASTE AND SENSORY IRRITATION OF SMOKELESS TOBACCO AND NON-TOBACCO PRODUCTS

CROSS-REFERENCE TO RELATED APPLICATIONS

This application claims priority to U.S. Provisional Patent Application Ser. No. 61/800,099, filed on Mar. 15, 2013, which is incorporated herein by reference in its entirety for all purposes.

BACKGROUND

In general, taste buds are known to react to all forms of stimuli, including sweet, sour, bitter, salt, and umami. Effective blocking of taste receptors can be accomplished by coating the surface pore or competing within channels to reduce the net effect of stimulation. The channels involved in taste perception are also associated with sensory irritation. Thus, technologies may be developed with flavor enhancing and analgesic properties by targeting channels and receptors involved in taste or sensory perception.

SUMMARY

Provided herein are tobacco products comprising a smokeless tobacco product and at least one active ingredient wherein the active ingredient is selected from, e.g., castor oil, ricinoleic acid, and conjugates or derivatives thereof, wherein the smokeless tobacco product is adapted to be chewed, sucked, or orally manipulated in a consumer's mouth. The at least one active ingredient may be hydrogenated ethoxylated glycerol ester or polyethoxylated hydrogenated castor oil.

Also provided herein are methods of making a tobacco product comprising combining a smokeless tobacco product with at least one active ingredient that is an antagonist of at least one receptor selected from the list consisting of nicotinic acetylcholine receptors, the TRPV1 channel, and the TRPA1 channel, wherein the at least one active ingredient is present in an amount effective to reduce or eliminate sensory irritation arising due to use of the product and wherein the at least one active ingredient is a taste receptor blocker. The active ingredient may be, e.g., castor oil, ricinoleic acid, esters of ricinoleic acid, oleic acid, linoleic acid, stearic acid, palmitic acid, dihydroxystearic acid, ricinelaidic acid, ricinolein, isopropyl ricinoleate, sodium ricinoleate, phenylacetylricinoleic acid, polyglycerol polyricinoleate, or derivatives and/or combinations thereof.

Also provided are analgesic compositions comprising a therapeutically effective amount of an active ingredient wherein the active ingredient is selected from, e.g., castor oil, hydrogenated ethoxylated glycerol ester, ricinoleic acid, esters of ricinoleic acid, ricinelaidic acid, ricinolein, isopropyl ricinoleate, sodium ricinoleate, polyethoxylated hydrogenated castor oil, phenylacetylricinoleic acid, polyglycerol polyricinoleate, and derivatives and/or combinations thereof. Such analgesic compositions may further comprise a smokeless tobacco product, an orally consumed non-tobacco product, a nicotine replacement therapy product, or a pharmaceutical composition. Such analgesic compositions may also comprise a pharmaceutical composition for treating chemical pain, physical irritation and/or disease-induced pain wherein the pharmaceutical composition may be administered by one of the routes selected from the group consisting of topically, orally, intranasally, by inhalation, and parenterally.

Also provided are liquid aerosol formulations for use in an electronic smoking article comprising at least one active ingredient, one aerosol former, optionally water, nicotine, and at least one acid. The at least one active ingredient may be hydrogenated ethoxylated glycerol ester or polyethoxylated hydrogenated castor oil. Preferably the at least one acid has a melting point and/or boiling point of at least about 150° C., such that the at least one acid volatilizes when heated by a heater of an electronic smoking article. Also preferably, the at least one acid is included in an amount sufficient to provide the liquid aerosol formulation to a pH ranging from about 4 to about 8. The liquid aerosol formulation is capable of forming an aerosol having a particle phase and a gas phase when heated. The particle phase contains protonated nicotine and the gas phase contains unprotonated nicotine. The aerosol has a majority amount of the protonated nicotine and a minority amount of the unprotonated nicotine.

In a preferred embodiment, the liquid aerosol formulation can include at least one flavorant in an amount ranging from about 0.2% to about 15% by weight. Moreover, the at least one aerosol former is selected from the group consisting of propylene glycol, glycerin and combinations thereof. Preferably, the at least one aerosol former is included in an amount ranging from about 40% by weight to about 90% by weight. In the preferred embodiment, the liquid aerosol formulation comprises glycerin and propylene glycol in a ratio of at least about 2:3.

In the preferred embodiment, the at least one acid has a boiling point and/or a melting point ranging from about 150° C. to about 250° C. Preferably, the at least one acid is included in an amount ranging from about 0.1% by weight to about 15% by weight. Also preferably, nicotine is included in an amount ranging from about 2% by weight to about 10% by weight. Moreover, the particle phase includes particles ranging in size from about 0.2 micron to about 2 microns.

Also provided are nicotine replacement therapies comprising a composition comprising a therapeutically effective amount of an active ingredient wherein the active ingredient is an antagonist of at least one receptor or channel selected from the list consisting of nicotinic acetylcholine receptors, the TRPV1 channel, and the TRPA1 channel.

Methods for reducing taste and sensory irritation of a composition are also provided, which comprise combining the composition with an effective amount of an active ingredient, such as castor oil, ricinoleic acid, esters of ricinoleic acid, ricinelaidic acid, ricinolein, isopropyl ricinoleate, sodium ricinoleate, phenylacetylricinoleic acid, polyglycerol polyricinoleate, and derivatives and/or combinations thereof.

DETAILED DESCRIPTION

Taste buds have been shown to respond to various forms of chemical stimuli. Effective blocking of taste receptors can be accomplished by inhibiting transportation of the chemical stimuli or by competitively inhibiting sensory ion channels to reduce the net effect of the chemical stimuli. In this way, taste sensations can be modified to reduce unpleasant or overwhelming flavor experience.

In addition to impacting taste sensations, chemical stimuli can also induce sensory irritations including pain, cooling, burning, itching, or other sensory irritations. As described herein, certain forms of taste-masking technology can be utilized to improve the taste experience and to concomitantly reduce, prevent, or eliminate sensory irritation resulting from chemical stimuli. In particular, nonionic solubilizers/emulsifying agents can be used to reduce or eliminate sensory irritation caused by chemical stimuli. In one embodiment of the present invention, the nonionic solubilizers/emulsifying agents can be incorporated into a smokeless tobacco product to reduce the sensory irritation caused by tobacco constituents, including nicotine, and to mask or diminish off-note flavors associated with consumption of the product. In another embodiment, the nonionic solubilizers/emulsifying agents can be incorporated in a non-tobacco orally enjoyable product, such as a caffeinated beverage or fruit juice, to reduce the sensory irritation of constituents contained therein, and to mask or diminish off-note flavors associated with consumption of the product. In another embodiment, the nonionic solubilizers/emulsifying agents can be used as an active ingredient in pharmaceutical compositions to act as an analgesic and to treat pain.

Definitions

As used herein, the term "portion" denotes an amount of a product that would typically be used by a consumer as an individual serving and/or dose. For example, a portion refers to a single pouch, film, strip, tab, lozenge, and/or other individual serving.

As used herein, the term "about" when used in conjunction with a stated numerical value or range denotes somewhat more or somewhat less than the stated value or range, to within a range of ±10% of that stated.

As used herein, the singular form "a," "an," and "the" include plural references unless the context clearly dictates otherwise. For example, the term "a cell" includes a plurality of cells, including mixtures thereof.

As used herein, the terms "particle" or "particles" denote any subdivided form of plant material (such as tobacco), and can include flakes, granules, powders, chopped stems, leaves, flowers, or other pieces, as well as extracts and derivatives thereof.

As used herein, the term "smokeless tobacco" denotes orally enjoyable tobacco products.

As used herein, the term "sensory irritation" includes itching, burning, and the like.

Active Ingredients

The present application is directed to active ingredients for modulating taste and sensory irritation in smokeless tobacco products, orally consumed non-tobacco products, liquid aerosol formulations for use in an electronic smoking article and for use in pharmaceutical compositions.

Active ingredients appropriate for use in the compositions described herein include castor oil, castor oil derivatives, and major components of castor oil. Non-limiting examples of castor oil derivatives include hydrogenated ethoxylated glycerol ester and polyethoxylated hydrogenated castor oil. Another major component of castor oil appropriate for use in the present application is ricinoleic acid, its derivatives, esters of ricinoleic acid, and analogs of ricinoleic acid. In one embodiment, the active ingredient is Cremophor® RH40, a commercially-available polyethylated castor oil and a known pharma-excipient that is tasteless, almost odorless, and soluble in a variety of solvents, including water. These compounds are particularly useful because they exhibit analgesic and anti-inflammatory effects in humans.

Other components of castor oil appropriate for use as active ingredients in the compositions described herein include oleic acid, linoleic acid, linolenic acid, stearic acid, palmitic acid, dihydroxystearic acid, and combinations and/or derivatives thereof. Without being bound to any particular theory, it is believed that these compounds provide sensory relief by inhibiting and/or or modulating nicotinic acetylcholine receptors (nAChRs), as well as transient receptor protein (TRP) ion channels such as the TRPV1 and TRPA1 channels on nociceptive fibers that mediate pain perception.

In one embodiment, the active ingredient is ricinoleic acid, castor oil, or the hydrogenated ethoxylated glycerol ester of ricinoleic acid. Ricinoleic acid (12-hydroxy-9-cis-octadecenoic acid) is an unsaturated omega-9 fatty acid that naturally occurs in mature Castor plant seeds or in sclerotium of ergot. About 90% of the fatty acid content in castor oil is the triglyceride formed from ricinoleic acid. Ricinoleic acid has been shown to have anti-inflammatory effects in experimental animal models. Ricinoleic acid can desensitize the TRPV1 channel which mediates the pain from heat and capsaicin, the hot principle of red pepper. Preliminary experiments show that application of nicotine in the mouth with a derivative of ricinoleic acid (Cremophor®) exhibited an analgesic effect in humans, including reduced burning in the mouth, throat, and esophagus and inhibition of the occurrence of hiccups. In addition, blister formation after heat application to the skin was also inhibited by Cremophor® compared to controls. Related active ingredients appropriate for use herein include ricinelaidic acid, ricinolein, isopropyl ricinoleate, sodium ricinoleate, phenylacetylricinoleic acid, polyglycerol polyricinoleate, and derivatives and/or combinations thereof.

In one embodiment, the active ingredients act directly on the receptors or channels where the pathological processes of disease or injury, or where any noxious matter is translated into nociception, pain and/or sensory irritation. In another embodiment, the active ingredients also exhibit anti-inflammatory activity in the periphery where the neuronal activity is translated into secretion of pro-inflammatory cytokines.

Active ingredients of the present application may be appropriate for use in any situation in which a nicotinic acetylcholine receptor, the TRPV1 channel or the TRPA1 channel is activated. Appropriate vehicles for use with the active ingredients described herein include smokeless tobacco products, orally consumed non-tobacco products, pharmaceutical compositions for the treatment of pain or disease related pathologies, and pharmaceutical compositions for the treatment of chemical or physical irritants.

In one embodiment, the active ingredient is capable of inhibiting the TRPV1 channel. In a further embodiment, the active ingredient is an active ingredient that inhibits the TRPA1 channel. In yet another embodiment, the active ingredient is an active ingredient that inhibits nicotinic acetylcholine receptors. In one embodiment, the composition includes at least two active ingredients. It will be understood that combinations appropriate for use in the present application may include more than two active ingredients. For example, one embodiment appropriate for use herein includes a combination of at least three active ingredients added to the composition. It will be further understood by those skilled in the art that active ingredients appropriate for use in the present application may function as an antagonist to one or more receptors. For example, ricinoleic acid may inhibit the nicotinic acetylcholine receptors and block the TRPV1 channel.

Active ingredients for use in the present application may be obtained in various commercially-available forms. In one embodiment, the active ingredient is obtained in a powder form. When obtained in a powder form, the active ingredient may be solubilized in a non-flavored oily carrier or other solution prior to being added to a product for use as particular applications may require.

Compositions of the present application contain at least one active ingredient. When a nicotinic acetylcholine receptor antagonist is used, it may be included in an amount ranging from about 0.01% to about 10% by weight based on the weight of the composition as determined on a per serving basis (e.g., about 0.05% to about 7.5%, about 0.1% to about 5%, about 0.5% to about 2.5%, about 1% to about 4%). When a TRPV1 antagonist is used, it may be included in an amount ranging from about 0.01% to about 10% by weight based on the weight of the composition as determined on a per serving basis (e.g., about 0.05% to about 7.5%, about 0.1% to about 5%, about 0.5% to about 2.5%, about 1% to about 4%). When a TRPA1 antagonist is used, it may be included in an amount ranging from about 0.01% to about 10% by weight based on the weight of the composition as determined on a per serving basis (e.g., about 0.05% to about 7.5%, about 0.1% to about 5%, about 0.5% to about 2.5%, about 1% to about 4%).

Compositions appropriate for use herein may also optionally include an acidic flavorant to interact with taste and channel receptors. In some embodiments, the acid is an organic acid. Common organic acids used as flavoring agents include citric acid, malic acid, pyruvic acid, acetic acid, oxalic acid, and lactic acid. One such acid appropriate for use with active ingredients of the present application is citric acid.

Nicotine

As described herein, products of the present application are contemplated to include nicotine and/or other sensory irritants found in tobacco-containing products. Nicotine, a chemical found in tobacco, produces effects in the body through the activation of neuronal nicotinic acetylcholine receptors. Nicotinic acetylcholine receptors are located on a variety of nerve endings in the peripheral nervous system and play a role in transmission of various sensations to the brain. For example and particularly relevant here, nicotinic acetylcholine receptors may signal a sense of irritation or burning to the brain. Nicotinic acetylcholine receptors are subdivided into two separate classes: N1 and N2. N1 receptors are located at the neuromuscular junction. N2 receptors play a key role in the transmission of cholinergic signals in the autonomic nervous system. These receptors can be found at the autonomic ganglia, the central nervous system, and the adrenal medulla. Nicotinic acetylcholine receptors are further subdivided according to the composition of their subunits. In humans, the subunits of nicotinic receptors belong to a 16 gene family.

Nicotine binds to nicotinic acetylcholine receptors, and subsequently triggers the release of neurotransmitters that produce psychoactive effects. In one embodiment, the smokeless tobacco product contains an active ingredient, such as ricinoleic acid, that when provided at sufficient concentrations, it will target the central nervous system to inhibit acetylcholine receptor activation by nicotine.

Nicotinic acetylcholine receptors exist in various conformational states. Agonists may bind to stabilize an open state. However, acetylcholine receptors can sometimes open with only one bound agonist and, even less frequently, with no agonist bound. Antagonists are also known to bind nicotinic acetylcholine receptors to inhibit their activity. Antagonists may be competitive inhibitors or non-competitive inhibitors.

In one embodiment, a smokeless tobacco product contains an active ingredient that acts as an antagonist that acts as a non-competitive inhibitor.

Smokeless Tobacco Products

Non-smokeable consumable products include smokeless tobacco products such as chewing tobacco, moist smokeless tobacco and dry snuff. When products containing a chemical irritant (e.g., an agonist of nicotinic acetylcholine receptors or of transient receptor protein ion channels such as the TRPV1 and/or TRPA1 channels), the products may cause undesirable sensory irritation and other undesired effects such as nausea.

Nicotinic acetylcholine receptors are located on a variety of nerve endings in the peripheral nervous system and play a role in transmission of sensations of irritation (e.g. burning) to the brain. As a result of activation of these receptors, consumers of some products, such as smokeless tobacco, sometimes experience irritation of the mouth, throat, esophagus, stomach, larynx, trachea, etc. when using a non-smokeable tobacco product. Nicotine and other agonists dissolve in the saliva, activate nicotinic acetylcholine receptors and/or sensitize vanilloid receptors, and thereby produce the undesired sensation where they contact the mucosa of the gastro-intestinal tract and of parts of the respiratory tract. The unwanted effects of these products go beyond sensory irritation (e.g., burning) and may include nausea, hiccups, and, in rare cases, vomiting.

By adding antagonists of such sensory receptors into a tobacco product, the perception of sensory irritation associated with consumption of that tobacco product may be reduced or eliminated. The active ingredients described herein preferably serve to reduce or eliminate sensory irritation arising from chemical irritants in consumable products containing tobacco and/or tobacco extracts. In addition, the active ingredients may also improve the flavor profiles experienced with those products during consumption.

Nicotine, for example, is an agonist of the nicotinic acetylcholine receptors, and can produce the sensory irritation, such as burning or stinging, in the mouth or throat, as well as the gastrointestinal discomfort sometimes associated with smokeless tobacco products. Active ingredients of the present application such as ricinoleic acid can effectively inhibit activation of sensory nerve fibers induced by nicotine. Thus, the addition of the active ingredients described herein, such as ricinoleic acid, to smokeless tobacco products can reduce the sensation of burning at the product location as well as along the path of saliva that had been in contact with the product. Moreover, the active ingredients can reduce undesirable and unpleasant sensations in the esophagus as well as nausea and hiccups.

In some embodiments of the smokeless tobacco product, higher concentrations of the active ingredient are employed to pass through the blood brain barrier. The effects of crossing the blood brain barrier are two-fold—to minimize the pleasurable aspects associated with smoking and to increase the bitterness sensed during smoking.

As described herein, portions of smokeless tobacco include pouched tobacco or components thereof and portions that are preferably free of a fabric and/or wrapper and comprise tobacco or components thereof that has been molded or divided into individual servings prior to use, such that portioned tobacco or components thereof can be placed in a consumer's mouth without the need for the consumer to determine an amount to use. Forms of portioned tobacco are described in, for example, commonly-assigned U.S. patent application Ser. Nos. 10/982,248; 11/626,176; 61/588,873;

61/720,852; 13/086,082; and 61/452,395, each of which is incorporated herein by reference in its entirety.

In one embodiment, the smokeless tobacco is in the form of a tab or bit. The addition of an active ingredient to a tab or bit of smokeless tobacco can reduce the sensation of burning at the tab or bit location as well as along the path of saliva that had been in contact with the tab or bit. Moreover, the active ingredient can reduce undesirable unpleasant sensations in the esophagus as well as nausea and hiccups.

When in the form of a tab or bit, an individual serving of the smokeless tobacco product preferably has a generally rectangular or elliptical shape. Other preferred shapes for the tab or bit include any shape selected from the group consisting of shields, polygons, squares, rectangles, circles, ovals, heart, star, half-moon, crescent, leaf shapes, and combinations thereof.

In another embodiment, the portion is sized and configured to fit inside the mouth, between a consumer's cheek and gum. Preferably, the portion takes a generally rectangular shape and is about 20 mm to about 35 mm long, about 10 mm to about 20 mm wide and about 3 mm to about 6 mm thick. The corners of the portion may be preferably rounded.

Preferably, the smokeless tobacco product weighs about 0.1 g to about 5.0 g. These ranges for weight can be further restricted to (a) about 0.1 g to about 1.0 g, (b) about 1.0 g to about 2.0 g, (c) about 2.0 g to about 3.0 g, (d) about 3.0 g to about 4.0 g or (e) about 4.0 g to about 5.0 g. Also preferably, the smokeless tobacco product 10 is 10 mm to about 20 mm in width, about 20 mm to about 40 mm in length, and about 5 mm to about 20 mm thick.

Preferably, the smokeless tobacco product is sized and configured to fit comfortably in a consumer's mouth. Preferably, the smokeless tobacco product delivers a plurality of flavor and/or functional ingredients to the consumer for a period of about one minute to about 1 hour. Preferably, the product may be discarded after a single use.

Some embodiments of a smokeless tobacco system include one or more preformed smokeless tobacco products configured to generally retain their shape during processing, shipping, and consumer handling. In particular embodiments, each smokeless tobacco product can include a moist smokeless tobacco in combination with a selected binder such that the preformed tobacco portion has improved handling, improved mouth feel, and satisfying flavor profile. Furthermore, some systems described can include a plurality of the smokeless tobacco products packaged into a container where each of the smokeless tobacco products has a substantially similar shape and provides a substantially similar, predetermined portion of tobacco to an adult tobacco consumer. Such a system can permit an adult tobacco consumer to receive consistent portions of tobacco (e.g., with each deposit of a product portion in the mouth) while also experiencing the tactile and flavor benefits of having the smokeless tobacco externally exposed on the article (e.g., not impeded by a paper-like pouch or sachet). Accordingly, some embodiments of the preformed smokeless tobacco product enable an adult tobacco consumer to handle each individual preformed piece from the container without the tobacco portion falling apart prior to placement in the adult tobacco consumer's mouth.

The tobacco, in some embodiments, is moist snuff. The tobacco can have a moisture content of at least 40 weight percent. In certain embodiments, the tobacco can include between 48 and 50 weight percent oven volatiles. The preformed smokeless tobacco products can, in some embodiments, have an oven volatiles content of between 50 and 61 weight percent (e.g., about 57 weight percent oven volatiles). In other embodiments, the tobacco can have a lower moisture content. For example, the total oven volatiles content for a preformed smokeless tobacco product can be between 10 and 30 weight percent.

Material Properties

In some embodiments, the material properties of the preformed smokeless tobacco product described herein can enhance tactility and flavor. In particular, the material properties improve handling, mouth feel, and flavor release. In certain embodiments, the material properties of one or more of the preformed smokeless tobacco products can be defined in terms of individual product friability, three point bend strength, and texture profile hardness.

Individual Product Friability

Friability is a measurement of the ability of an object to be reduced to smaller pieces when subjected to pressure or friction. A numerical value for friability is dependent on the specific test used. As used herein, "individual product friability" is the weight percent of material lost due to the placement of an individual product within a friability drum and rotated at 25 rpm for 100 revolutions, which is equal to four (4) minutes of rotation. A friability drum is a standard friability drum with a diameter of 152 mm. For example, a standard friability drum meeting USP, EUR, and DAB pharmacopoeia standards, such as the Erweka GmbH D63159 friability tester having a standard USP 100 Method friability drum, can be used to test the preformed smokeless tobacco product. In particular embodiments, a plurality of preformed smokeless tobacco products have an average individual product friability of between 0.5 weight percent and 80 weight percent. The individual product friability of each preformed smokeless tobacco product is, in some embodiments, between 1.0 weight percent and 10 weight percent. For example, the individual product friability of each preformed smokeless tobacco product can be between 1.7 weight percent and 2.1 weight percent.

The preformed smokeless tobacco product can have an individual product friability of less than 80 weight percent to increase the likelihood that each of the products can be packaged, shipped, stocked, purchased, carried, and handled prior to use without significantly falling apart or otherwise significantly deteriorating from its original shape and tobacco content. After packaging, the container retaining each preformed smokeless tobacco product may be subjected to rotated, being dropped or otherwise moved around in a jarring manner during shipping and stocking of the product. Adult tobacco consumers may also move the container in a jarring manner during ordinary usage. Moreover, the plurality of preformed tobacco products in the container may shift and move against each other during any jarring movement. Additionally, as products are individually removed from the container, the risk of fragmenting increases as the remaining preformed smokeless tobacco products have more room for motion relative to the container within the interior space. In some embodiments, the preformed smokeless tobacco product has an individual product friability of less than 60 weight percent. The preformed smokeless tobacco product can also have an individual product friability of less than 50 weight percent. In some embodiments, the preformed smokeless tobacco product has an individual product friability of less than 40 weight percent. In still other embodiments, the preformed smokeless tobacco product has an individual product friability of less than 30 weight percent. In still other embodiments, the preformed smokeless tobacco product has an individual product friability of less than 20 weight percent. The preformed smokeless tobacco product can also have an individual product friability of less than 10 weight percent. The individual product friability of each preformed smokeless tobacco product can also be less than 7 weight percent. In some embodiments, the individual product friability of each preformed smokeless tobacco product is less than 4 weight percent. For example, the individual product friability of each preformed smokeless tobacco product can be less than 2.1 weight percent.

The preformed smokeless tobacco product may have an individual product friability of at least 0.5 weight percent to increase the likelihood of a good mouth feel and flavor release. Although a non-friable product (e.g., a product having an individual product friability of approximately zero) can be placed in an adult tobacco consumer's mouth, a non-friable product does not provide a mouth feel or flavor release that is similar to loose smokeless tobacco. Accordingly, in particular embodiments, an individual product friability of at least 0.5 weight percent can allow the product to partially conform to the contours of an adult tobacco consumer's mouth (e.g., to the contours between a lip and a gingiva). An individual product friability of at least 0.5 weight percent can also permit different portions of the tobacco within the product to make contact with the adult tobacco consumer's oral cavity. In some embodiments, the preformed smokeless tobacco product has an individual product friability of at least 1.0 weight percent. In still other embodiments, the preformed smokeless tobacco product has an individual product friability of at least 1.5 weight percent. For example, the individual product friability of each preformed smokeless tobacco product can be greater than 1.7 weight percent.

Three Point Bend Strength

Three Point Bend ("TPB") strength is a measurement of the force required to break a shaped smokeless tobacco body into two or more pieces. The TPB strength is determined using a TPB test. The TPB test places a shaped smokeless tobacco body lengthwise across two supports. The shaped smokeless tobacco body has a length (e.g., a maximum dimension). The supports are spaced at a distance that is approximately half of the length of the shaped smokeless tobacco body. Accordingly, the spacing between supports is adjusted depending on the length of the shaped smokeless tobacco body being tested. The lengthwise midpoint of the shaped smokeless tobacco body is positioned at the midpoint of the distance between the two supports. During the TPB test, an angled compression jig presses against the lengthwise midpoint of the shaped smokeless tobacco body with increasing force using a stroke rate of 155 mm/minute. The angled compression jig has a 2 mm thickness and a 50 mm width. The TPB strength is the force used with the angled compressing jig that causes the shaped smokeless tobacco body to break.

As used herein, "three point bend strength" is the force required to break the product using the TPB test described herein. In some embodiments, the preformed smokeless tobacco product described herein can have a TPB strength of at least 0.25 N to reduce the likelihood that the product falls apart prior to oral usage. In some embodiments, the preformed smokeless tobacco product has a TPB strength of less than 4.0 N. In some embodiments, the preformed smokeless tobacco product has a TPB strength of less than 2.0 N. In some embodiments, the preformed smokeless tobacco product has a TPB strength of between 0.25 N and 0.8 N.

Hardness

A hardness measurement can be used to describe the force required to deform the preformed smokeless tobacco product. For example, a tensile profile hardness test can measure hardness by creating a particular indentation by pressing a sphere into the tested sample. The Hardness measurement can be a component of the Texture Profile Analysis (TPA) test that is sometimes used to evaluate various consumer products. The TPA test is performed by placing the sample on a flat surface (side with largest surface facing down) and compressing the sample with a 10 mm round ball fixture 3.5 mm (50% of sample thickness) into the sample surface. Once the 3.5 mm depth is achieved, the compression jig is immediately raised at the same stroke speed to the zero-stroke position (the starting position). The compression fixture is then lowered to repeat the exact same compression sequence a second time. The load applied to the round ball compressing jig is increased until an indentation of 3.5 mm is made. Between compression events, the compressing jig is held at the zero-stroke position for 30 seconds. As used herein, "texture profile hardness" is the maximum force achieved during an initial process of pressing a 10 mm round ball compression jig (e.g., of stainless steel) 3.5 mm into the surface of a sample for a 30 second hold time using a stroke rate of 50 mm/min. The forces measured during the second compression of a TPA test are compared to the forces achieved during the first compression to calculate the additional metrics of springiness and cohesiveness.

In particular embodiments, the preformed smokeless tobacco product can have a texture profile hardness of at least 2.0 to reduce the likelihood that the product substantially deforms in response to jarring movements of the container. In some embodiments, the preformed smokeless tobacco product has a texture profile hardness of at least 4.0 N. In still other embodiments, the preformed smokeless tobacco product has a texture profile hardness of at least 4.5 N. The texture profile hardness can also be greater than 5.0 N.

The preformed smokeless tobacco product can have a texture profile hardness of less than 12.0 N to increase the likelihood that each product can be readily conformed to surfaces within an adult tobacco consumer's mouth. For example, after insertion of the product into the mouth, the adult tobacco consumer can press the preformed smokeless tobacco product between a lip and the gingiva to conform the product to the contours of the gingiva and the lip. In some embodiments, the preformed smokeless tobacco product has a texture profile hardness of less than 8.0. The texture profile hardness of each preformed smokeless tobacco product can also be less than 5.5. For example, the preformed smokeless tobacco product can have a texture profile hardness of between 4.5 N and 5.5 N to balance the need to have a product that retains its shape during transport but one that can also be readily reshaped after placement in an adult tobacco consumer's mouth.

Product Constituents

The tobacco material may be provided in any suitable form, including shreds and/or particles of tobacco lamina, processed tobacco materials, such as volume expanded or puffed tobacco, or ground tobacco, processed tobacco stems, such as cut-rolled or cut-puffed stems, reconstituted tobacco materials, tobacco beads, blends thereof, and the like. Genetically modified tobacco and other treated tobaccos may also be used in the filling material. Also, preferably, the tobacco material is smaller than about mesh for ease of pouching.

The tobacco is any tobacco suitable for use in the smokeless tobacco product. By "tobacco" it is meant a part, e.g., leaves, flowers, and stems, of a member of the genus *Nicotiana*. Exemplary species of tobacco include *N. rustica*,

*N. tabacum, N. tomentosiformis*, and *N. sylvestris*. Suitable tobaccos include fermented and unfermented tobaccos, dark air-cured, dark fire-cured, burley, flue cured, and cigar filler or wrapper, as well as the products from the whole leaf stemming operation. For example, tobacco can be conditioned by heating, sweating and/or pasteurizing steps as described in U.S. Publication Nos. 2004/0118422 or 2005/0178398. Fermenting typically is characterized by high initial moisture content, heat generation, and a 10 to 20% loss of dry weight. See e.g., U.S. Pat. Nos. 4,528,993; 4,660,577; 4,848,373; and 5,372,149. In addition to modifying the aroma of the leaf, fermentation can change either or both the color and texture of a leaf. Also during the fermentation process, evolution gases can be produced, oxygen can be taken up, the pH can change, and the amount of water retained can change. See, for example, U.S. Publication No. 2005/0178398 and Tso (1999, Chapter 1 in Tobacco: Production, Chemistry and Technology, Davis & Nielsen, eds., Blackwell Publishing, Oxford). Cured, or cured and fermented tobacco can be further processed (e.g., cut, expanded, blended, milled or comminuted) prior to incorporation into a preformed smokeless tobacco product. The tobacco, in some embodiments, is cured long cut fermented moist tobacco having an oven volatiles content of between 48 and 50 weight percent prior to mixing with the binder and optionally flavorants and/or other additives.

In some embodiments, the tobacco can be prepared from or include leaf tobacco from tobacco plants having less than 20 µg of DVT per cm2 of green leaf tissue, For example, the tobacco can be selected from the tobaccos described in U.S. Patent Publication No. 2008/0209586, which is hereby incorporated by reference. Tobacco compositions containing tobacco from such low-DVT varieties exhibit improved flavor characteristics in sensory panel evaluations when compared to tobacco or tobacco compositions that do not have reduced levels of DVTs.

In some embodiments, the product may be a nicotine-containing lozenge. Nicotine-containing lozenges appropriate for use herein may be formed by a polymer matrix. In one embodiment, the nicotine-containing lozenge contains up to about 1.5 mg of nicotine. In one embodiment, the nicotine-containing lozenge is a chewable lozenge. In one embodiment, the nicotine-containing lozenge contains tobacco-derived nicotine, non-tobacco cellulose fibers, and a polymer. Polymers appropriate for use herein include all synthetic polymers. In some embodiments, the polymers may be polyurethane or polyvinyl. The nicotine-containing lozenge may optionally include flavorants.

In one embodiment, in addition to or in lieu of tobacco material, the filling material can also include a supplemental amount of botanical material other than tobacco, such as tea, coffee, herbs, spices, and/or vegetable fibers. Additionally, the tobacco material may also include a supplemental amount of vegetable or plant fibers or particles, such as particles of shreds of lettuce, cotton, flax, beet fiber, cellulosic fibers, blends thereof, and the like.

In another embodiment, additives can also be added to the filling material and/or pouch wrapper of the oral tobacco pouch product. Suitable additives include, without limitation, humectants, flavorants, sweeteners, and/or combinations thereof.

In some embodiments, the one or more smokeless tobacco products include at least 0.5 weight percent of binder. The smokeless tobacco products can, in some embodiments, include less than 5.0 weight percent binder. In certain embodiments, the smokeless tobacco products include between 0.5 and 1.5 weight percent binder.

The binder can be a carbohydrate. In some embodiments, the binder includes a hydroxyl containing compound, a dextrin or dextrin derivative, carboxymethyl cellulose, hydroxypropyl cellulose, hydroxyethyl cellulose, hydroxypropyl methyl cellulose, methyl cellulose, konjac, collagen, inulin, soy protein, casein, wheat gluten, carrageenan, alginates, propylene glycol alginate, xanthan, dextrin, pullulan, curdlan, gellan, locust bean gum, guar gum, tara gum, gum tragacanth, pectin, agar, zein, karaya, gelatin, psyllium seed, chitin, chitosan, gum acacia, polyvinyl pyrrolidone, polyethylene oxide, polyvinyl alcohol, or a combination thereof. In certain embodiments, the binder is selected from the group of guar gum, xanthan, cellulose, and combinations thereof. For example, the preformed smokeless tobacco products can include between 0.6 and 0.8 weight percent of a binder that includes guar gum, xanthan, and cellulose.

In some embodiments, the preformed smokeless tobacco product can optionally include one or more flavorants. For example, suitable flavorants include wintergreen, cherry and berry type flavorants, various liqueurs, and liquors such as DRAMBUIE, bourbon, scotch, whiskey, spearmint, peppermint, lavender, cinnamon, cardamon, apium graveolents, clove, cascarilla, nutmeg, sandalwood, bergamot, geranium, honey essence, rose oil, vanilla, lemon oil, orange oil, Japanese mint, cassia, caraway, cognac, jasmine, chamomile, menthol, ilangilang, sage, fennel, piment, ginger, anise, coriander, coffee, liquorice, and mint oils from a species of the genus *Mentha*. Mint oils useful in particular embodiments of the smokeless tobacco product include spearmint and peppermint.

The smokeless tobacco product may optionally include other additives. Other additives include fillers (e.g., starch, di-calcium phosphate, lactose, sorbitol, mannitol, and microcrystalline cellulose), soluble fiber (e.g., FIBERSOL from Matsushita), calcium carbonate, dicalcium phosphate, calcium sulfate, and clays), lubricants (e.g., lecithin, stearic acid, hydrogenated vegetable oil, mineral oil, polyethylene glycol 4000-6000 (PEG), sodium lauryl sulfate (SLS), glyceryl palmitostearate, sodium benzoate, sodium stearyl fumarate, talc, and stearates (e.g., Mg or K), and waxes (e.g., glycerol monostearate, propylene glycol monostearate, and acetylated monoglycerides), plasticizers (e.g., glycerine, propylene glycol, polyethylene glycol, sorbitol, mannitol, triacetin, and 1, 3 butane diol), stabilizers (e.g., ascorbic acid and monosterol citrate, BHT, or BHA), artificial sweeteners (e.g., sucralose, saccharin, and aspartame), disintegrating agents (e.g., starch, sodium starch glycolate, cross caramellose, cross linked PVP, pH stabilizers, or other compounds (e.g., vegetable oils, surfactants, and preservatives). Some compounds display functional attributes that fall into more than one of these categories. For example, propylene glycol can act as both a plasticizer and a lubricant and sorbitol can act as both a filler and a plasticizer. Water and other oven volatiles can also be added during a mixing process (discussed below) to alter the total oven volatiles content of the formed smokeless tobacco product. Various salts can also be added.

The type and amount of flavorants and other additives can also impact the material properties of the smokeless tobacco product. In some embodiments, the amount of flavorants and other additives in the preformed smokeless tobacco product are limited to less than 10 weight percent in sum. In some embodiments, the amount of flavorants in the preformed smokeless tobacco product are limited to be less than 5 weight percent in sum. For example, certain flavorants can be included in the preformed smokeless tobacco product in amounts of about 3 weight percent.

In some embodiments, the combination of tobacco, flavorants, and other additives used in the preformed smokeless tobacco product can be the mixture of tobacco, flavorants, and other additives commercially sold as smokeless tobacco. For example, the finished tobacco can be the same as the finished smokeless tobacco sold under the trade name SKOAL (e.g., SKOAL Long Cut), which includes flavorants and other additives.

Nicotine Replacement Therapies

Active ingredients of the present application may also be used in combination with nicotine replacement therapies. In one embodiment, ricinoleic acid, castor oil or the hydrogenated ethoxylated ester of ricinoleic acid is used as an active ingredient in a nicotine replacement therapy.

When used in nicotine replacement therapies, the active ingredients described herein reduce or eliminate peripheral side effects of the nicotine replacement therapies typically associated with reduced treatment compliance, thereby enhancing the effectiveness of the nicotine replacement therapy.

In one embodiment, the nicotine replacement therapy is administered orally through the mouth. For example, the nicotine replacement therapy may be a chewing gum that contains nicotine and an active ingredient. In another embodiment, the nicotine replacement therapy is administered as a spray or by an inhaler. When used as a spray or by an inhaler, the active ingredient may provide the additional benefit of decreasing the sensation of burning in the nose or throat caused by the spray. In a further embodiment, the nicotine replacement therapy may be administered to the skin. For example, the nicotine replacement therapy may be a nicotine patch. When used in a patch, the active ingredient may provide the additional benefit of reducing skin inflammation (i.e., redness and irritability) at the site of application.

Analgesic Properties

Active ingredients of the present application may also be used in pharmaceutical compositions to treat chemical and physical irritation and/or pathological pain and pathological irritation associated with disease. In one embodiment, the active ingredients are formulated as an ointment to treat skin pain. In another embodiment, the active ingredients are formulated as a pharmaceutical composition to treat mucosal pain and inflammation. Appropriate areas for use include the mouth, nose, respiratory tract, esophagus, and vagina. In yet another embodiment, the active ingredients are formulated in a pharmaceutical composition for systemic enteral administration for acute and chronic pain states with and without inflammation. In a further embodiment, the active ingredients are formulated in a pharmaceutical composition for systemic parenteral application to treat acute pain states. In another embodiment, the active ingredients are formulated for topical parenteral applications. In another embodiment, the active ingredients are formulated in a sprayable composition for treating large areas of skin damage, such as those caused by heat.

Because the active ingredients of the present application are not COX inhibitors, the potential for unwanted side effects such as blood clotting and gastric mucosa or kidney damage may be lower compared to other analgesics or local anesthetics.

Packaging

Individual compositions will be packaged as appropriate for the contents of the composition. Preferably, the compositions are stored in a waterproof case and are stable between 40 and 120° F. Compositions are typically dry, flexible, and non-adhesive while in storage. Alternatively, compositions may be packaged using non-stick barriers, e.g., plastic film or paper, between servings. Compositions may also be provided in a bulk form, from which individual servings are separated.

In another embodiment, the package is water impermeable and water insoluble. In yet another embodiment the package is water impermeable and water insoluble, and tobacco, e.g., in liquid, slurry, or flowable gel form, is disposed within the package, e.g., a squeezable plastic package, a bellows, or a spray bottle, and is capable of being dispensed into the mouth from the package. The bellows may be compressed for oral use. Solutions or slurries are prepared for use in a plastic bellows container or other similar consumer packaging containers wherein the liquid is injected into the mouth by squeezing the package. Thixotropic polymers are combined with tobacco and other ingredients to prepare higher viscosity solutions suitable for use in other containers. Tobacco particles can be of greater size, but must still be small enough to pass through the orifice of the container. For spray bottles, a pharmaceutical composition or a stable tobacco slurry is contained in the bottle; tobacco particles are sized to be able to pass through a spray nozzle without blocking the orifice; and the tobacco slurry is sprayed directly in the oral cavity. Liquid sprays are prepared by dissolving a thixotropic polymer such as xanthan, gellan or dextran in water and suspending tobacco particles in a low viscosity (e.g., <50 centipoise) solution. Other compounds, such as flavor, sweetener and dispersant, can be added to the solution. The tobacco particles are ground to a particle size (e.g., <80 microns) to permit the homogeneous solution to pass through the orifice of a spray bottle. Other packages may be otherwise squeezed or used to expel the composition into the oral cavity.

Electronic Smoking Articles

In another embodiment, the liquid aerosol formulation for use in each of the electronic smoking or vaping articles described herein includes at least one active ingredient of the present application, one aerosol former, water, a nicotine source, and at least one acid.

In the preferred embodiment, the at least one aerosol former is selected from the group consisting of propylene glycol, glycerin and combinations thereof. Preferably, the at least one aerosol former is included in an amount ranging from about 40% by weight based on the weight of the liquid formulation to about 90% by weight based on the weight of the liquid formulation (e.g., about 50% to about 80%, about 55% to about 75% or about 60% to about 70%). Moreover, in one embodiment, the liquid formulation can include propylene glycol and glycerin included in a ratio of about 3:2.

Preferably, the liquid formulation also includes water. Water can be included in an amount ranging from about 5% by weight based on the weight of the liquid formulation to about 40% by weight based on the weight of the liquid formulation, more preferably in an amount ranging from about 10% by weight based on the weight of the liquid formulation to about 15% by weight based on the weight of the liquid formulation.

The liquid aerosol formulation optionally includes at least one flavorant in an amount ranging from about 0.2% to about 15% by weight (e.g., about 1% to about 12%, about 2% to about 10%, or about 5% to about 8%). The at least one flavorant can be a natural flavorant or an artificial flavorant. Preferably, the at least one flavorant is selected from the group consisting of tobacco flavor, menthol, wintergreen, peppermint, herb flavors, fruit flavors, nut flavors, liquor flavors, and combinations thereof.

Also preferably, the liquid aerosol formulation includes at least one acid having a melting point and/or a boiling point of at least about 150° C. For example, the at least one acid can have a melting point and/or a boiling point ranging from about 150° C. to about 300° C., more preferably about 150° C. to about 250° C. (e.g., about 160° C. to about 240° C., about 170° C. to about 230° C., about 180° C. to about 220° C. or about 190° C. to about 210° C.). By including at least one acid having a melting point and/or a boiling point within this range, the at least one acid may volatilize when heated by heater elements of electronic smoking or vaping articles as previously described. In an embodiment utilizing a heater coil and a wick, the heater coil may reach an operating temperature at or about 300° C.

Also preferably, the at least one acid is included in the liquid aerosol formulation in an amount sufficient to reduce the pH of the liquid aerosol formulation to a pH ranging from about 4 to about 8, more preferably about 5 to about 7 or about 5.5 to about 6.5. Moreover, the at least one acid is preferably condensable at ambient temperature.

Suitable acids for use in the liquid aerosol formulation include, without limitation, succinic acid, tartaric acid, sulfuric acid, carbonic acid, malonic acid, tartronic acid, levulinic acid, acetic acid, benzoic acid, adipic acid, gluaric acid, pimelic acid and combinations thereof. Preferably, the at least one acid is included in an amount ranging from about 0.1% by weight to about 15% by weight (e.g., about 1% to about 12%, about 2% to about 10%, about 3% to about 9% or about 4% to about 8%).

The amount of acid added to the liquid aerosol formulation may depend on the strength of the acid and the amount needed to adjust the pH of the liquid aerosol formulation to the desired range. If too much acid is added, essentially all of the available nicotine will be protonated and will enter the particle phase of the aerosol, leaving very little unprotonated nicotine in the gas phase of the aerosol. The resultant aerosol may not produce sufficient levels of sensory response in terms of throat harshness to meet preferences of a smoker of lit-end cigarettes. In contrast, if too little acid is added, a larger amount of nicotine will remain unprotonated and in the gas phase of the aerosol, such that the smoker will experience increased throat harshness. With liquid formulations of nicotine content above approximately 2% by weight, and in the absence of addition of an acid according to the teachings herein, perceived throat harshness may approach levels which render the aerosol as unpleasant to inhale, and with liquid formulations of nicotine content above approximately 4% by weight, and in the absence of an acid according to the teachings herein, perceived throat harshness may approach levels rendering the aerosol uninhalable. With the addition of an acid according to the teachings herein, perceived throat harshness is maintained at desirable levels, akin to that experienced with lit-end cigarettes.

Preferably, the liquid aerosol formulation also includes at least one nicotine source. The nicotine is included in the liquid aerosol formulation in an amount ranging from about 1% by weight to about 10% by weight (e.g., about 2% to about 9%, about 2% to about 8%, about 2% to about 6%).

In one embodiment, the nicotine source can comprise molecular (unprotonated) nicotine. Typically, molecular nicotine in an aqueous solution has a pH of about 9 to about 10. Thus, the at least one acid would need to be added in an amount sufficient to reduce the pH to about 4 to about 8. In an embodiment, molecular (unprotonated) nicotine is added in liquid form.

In an alternative embodiment, the nicotine source can comprise one or more nicotine salts, which can be added to a formulation to provide both the nicotine and the at least one acid. The nicotine salt can be a salt of succinic acid, tartaric acid, sulfuric acid, carbonic acid, malonic acid, tartronic acid, levulinic acid, acetic acid, benzoic acid, adipic acid, gluaric acid, pimelic acid and combinations thereof. A preferred nicotine-acid salt is nicotine bitartrate.

When vaporized in the electronic smoking article, the liquid aerosol formulation is capable of forming an aerosol having a particle phase and a gas phase. Preferably, the particle phase contains protonated nicotine and the gas phase contains unprotonated nicotine. Also preferably, the majority of nicotine is protonated and in the particle phase, while a minority amount of nicotine is contained in the gas phase. Once the liquid aerosol formulation has been vaporized, the vapor condenses, nicotine is protonated and particles including the protonated nicotine are formed. A minor amount of the nicotine remains unprotonated and stays in the gas phase of the newly generated aerosol. Preferably, because of the addition the acid, about 0.1 to about 1.0% of the total nicotine content of the aerosol is believed to be unprotonated (e.g., about 0.2% to about 0.7% or about 0.3% to about 0.5%), while the remainder of the available nicotine is believed to be delivered in a protonated (charged) form and in the particulate phase. Preferably, the particle phase includes particles ranging in size from about 0.2 micron to about 2 microns.

EXAMPLES

Example 1

Cremophor® RH40 (8% treat rate) was injected into approximately 1.1 g SKOAL Snus pouches (smooth mint) and carefully mixed with the material inside the pouch. The modified pouches resulted in reduced sensory irritation relative to normal, untreated pouches.

Example 2

Chewable formulations containing nicotine were prepared with the combination of the active ingredient Cremophor® in the presence and absence of citric acid. Individuals were queried as to the their sensory irritation experience. As can be seen in the chart below, Cremophor® alone reduced sensory irritation. Moreover, the combination of Cremophor® and citric acid eviscerated sensory irritation.

| Expt. # | Chewable Formulation (Containing 25% less salt SKOAL WG recombinant) Weight, mg | Nicotine Content mg | Cremophor RH40, % based on total formulation | Citric Acid, % based on total formulation | Preliminary Evaluation Findings, Irritation Level |
|---|---|---|---|---|---|
| 1 | 650 | 2 | 8 | 0 | Present but reduced |
| 2 | 650 | 2 | 5 | 0 | Present but reduced |

| Expt. # | Chewable Formulation (Containing 25% less salt SKOAL WG recombinant) Weight, mg | Nicotine Content mg | Cremophor RH40, % based on total formulation | Citric Acid, % based on total formulation | Preliminary Evaluation Findings, Irritation Level |
|---|---|---|---|---|---|
| 3 | 650 | 2 | 0 | 3 | Present, NOT reduced |
| 4 | 650 | 2 | 8 | 3 | No irritation |
| 5 | 650 | 4 | 8 | 0 | Present but reduced |
| 6 | 650 | 4 | 5 | 0 | Present but reduced |
| 7 | 650 | 4 | 8 | 3 | No irritation |
| 8 | 650 | 4 | 3 | 3 | Present |

Example 3

Liquid formulations were prepared by combining caffeinated water or commercially available grapefruit juice with Cremophor® alone, citric acid alone or the combination of Cremophor® and citric acid. At low levels, Cremophor® alone and citric acid alone had little noticeable effect on the perceived bitterness of the caffeinated water formulation. However, when tested with the combination of Cremophor® and citric acid, perceived bitterness levels were eliminated. In the commercial grapefruit juice formulations, the addition of Cremophor® at three difference concentrations resulted in the elimination of perceived bitterness levels. Because grapefruit juice naturally contains citric acid, citric acid was not added to the grapefruit juice formulations.

| Expt. # | Liquid Formulation with bitter compound | Cremophor RH40, % based on total formulation | Citric Acid, % based on total formulation | Preliminary Evaluation Findings, Bitterness Level |
|---|---|---|---|---|
| 1 | 100 mL of water containing 225 mg Caffeine | 2 | 0 | Still bitter |
| 2 | 100 mL of water containing 225 mg Caffeine | 0 | 2 | Still bitter |
| 3 | 100 mL of water containing 225 mg Caffeine | 2 | 2 | Not bitter, palatable |
| 4 | 100 mL of commercial grapefruit juice | 2 | 0 | Not bitter, palatable |
| 5 | 100 mL of commercial grapefruit juice | 8 | 0 | Not bitter, palatable |
| 6 | 100 mL of commercial grapefruit juice | 8 | 0 | Not bitter, palatable |

Example 4

Polyoxyl 40 hydrogenated castor oil, a polyethoxylated hydrogenated castor oil, was used in liquid formulation at various concentrations of 0.05%, 0.5%, and 1%. The ingredient at a desired concentration was introduced by dissolving the same in the formulation containing flavor, diluent, and nicotine. The sensory profile was affected depending on the concentration of the ingredient.

It is to be understood that, while the systems, products, compositions of matter, and methods have been described herein in conjunction with a number of different embodiments, the foregoing description of the various embodiments is intended to illustrate and not limit the scope of the systems, products, compositions of matter, and methods. Other embodiments, advantages, and modifications are within the scope of the following claims. All publications cited herein are incorporated herein by reference in their entirety for all purposes.

What is claimed is:

1. A tobacco product comprising:
   a smokeless tobacco product;
   at least one active ingredient selected from the group consisting of hydrogenated ethoxylated glycerol ester, ricinoleic acid, and conjugates or analogs thereof,
   a flavorant, and
   a coating on an external surface of the smokeless tobacco product,
   wherein the smokeless tobacco product is adapted to be chewed, sucked, or orally manipulated in a consumer's mouth,
   wherein the smokeless tobacco product is selected from the group consisting of a pouch including a plurality of pores, a lozenge comprising a synthetic polymer, and a chewing gum,
   wherein the active ingredient is about 0.1% to about 10% by weight based on the weight of the tobacco product,
   wherein the at least one active ingredient is found in a soluble portion of said coating, and wherein the smokeless tobacco product has an individual product friability of less than 2.1 weight percent, a three point bend strength of at least 0.25 N and less than 4.0 N, and a texture profile hardness of at least 2.0 N and less than 12.0 N.

2. The tobacco product of claim 1, wherein the product further comprises an additive selected from one or more of preservatives, binder, pH stabilizers, disintegrating agents, cross-linking agents, botanical material, vegetable fibers, sweeteners, humectants, and a combination thereof.

3. The tobacco product of claim 1, wherein the flavorant is an organic acid flavorant selected from one or more of citric acid, malic acid, pyruvic acid, acetic acid, oxalic acid, lactic acid, and a combination thereof.

* * * * *